United States Patent [19]
Rosenberg

[11] Patent Number: 5,630,843
[45] Date of Patent: May 20, 1997

[54] DOUBLE CHAMBER TISSUE EXPANDER

[76] Inventor: Paul H. Rosenberg, 1600 Parker Ave. #27D, Fort Lee, N.J. 10021

[21] Appl. No.: 268,508
[22] Filed: Jun. 30, 1994
[51] Int. Cl.$^6$ ..................................... A61F 2/12
[52] U.S. Cl. .................. 623/8; 604/890.1; 604/891.1; 604/101
[58] Field of Search ............... 623/8; 604/890.1, 604/891.1, 101; 606/191, 192; 600/31

[56] References Cited

U.S. PATENT DOCUMENTS

| | | |
|---|---|---|
| 2,499,045 | 2/1950 | Walker . |
| 3,765,414 | 10/1973 | Arlen . |
| 3,934,274 | 1/1976 | Hartley et al. . |
| 4,685,447 | 8/1987 | Iversen et al. . |
| 4,692,146 | 9/1987 | Hilger ..................... 604/890.1 |
| 4,800,901 | 1/1989 | Rosenberg . |
| 4,840,615 | 6/1989 | Hancock et al. ............. 604/93 |
| 4,984,585 | 1/1991 | Austad . |
| 5,005,591 | 4/1991 | Austad . |
| 5,042,976 | 8/1991 | Ishitsu et al. .............. 604/96 |
| 5,049,132 | 9/1991 | Shaffer et al. ............. 604/101 |
| 5,100,392 | 3/1992 | Orth et al. . |
| 5,141,508 | 8/1992 | Bark et al. ................ 623/8 |
| 5,295,962 | 3/1994 | Crocker et al. ............ 604/101 |
| 5,318,531 | 6/1994 | Leone ..................... 604/101 |
| 5,380,319 | 1/1995 | Saito et al. ............... 604/101 |

Primary Examiner—John G. Weiss
Assistant Examiner—Bruce E. Snow
Attorney, Agent, or Firm—Klauber & Jackson

[57] ABSTRACT

A tissue expansion device for subcutaneous implantation in a patient consisting of an implantable expandable bladder prepared from a porous material which defines an infusion solution chamber, and an inner bladder disposed within the outer bladder prepared from an expandable non-porous material which defines an expansion solution chamber. Liquid transport means are provided for introducing and removing an infusion solution into and out of the infusion solution chamber, and fluid transport means are provided for introducing and removing an expansion fluid into and out of the expansion solution chamber. Following implantation of the tissue expansion device subcutaneously, expansion fluid can be introduced into the expansion chamber by use of the fluid transport means causing the inner bladder to expand. The expansion of the inner bladder exerts pressure on the infusion chamber, which contains infusion solution introduced through the liquid transport means. The infusion solution passes through the pores of the expandable porous material into the tissue surrounding and contacting the expansile porous wall of the implanted tissue expansion device. The outer bladder also expands, due primarily to expansion of the inner bladder and to introduction of infusion solution. The infusion solution can contain agents to facilitate the expansion process, such as hyaluronidase, lidocaine, epidermal growth factor, or dexamethasone, or any combination thereof.

14 Claims, 5 Drawing Sheets

DOUBLE CHAMBER TISSUE EXPANDER

FIELD OF THE INVENTION

The present invention relates to a device for the expansion of tissue, in particular, to an implantable tissue expander which provides for a liquid solution to diffuse into the subcutaneous tissue in contact with or proximity to the expansile (or expansible) surface of the implanted device.

BACKGROUND OF THE INVENTION

In the field of reconstructive surgery, tissue expanders play an important role. Mechanical tissue expansion is a means to increase the dimensions of tissue. The technique is commonly used in surgery involving the implantation of permanent prosthetics, such as breast reconstruction, and reconstructive surgery in which additional skin is required, such as burn reconstruction.

Tissue expansion for cosmetic or reconstructive surgery has two components: dissection of the skin and subdermal elements from the underlying tissue, to create a cavity, and expansion of an expander device placed in the cavity to stretch the surrounding tissues, particularly the skin. The dissection process may continue after implantation of an expander, thus recruiting additional tissue to stretch in response to the force of the expander.

The expansion of tissue can be a painful procedure, require long time periods, or both. Furthermore, the success of a tissue expansion procedure will depend on the characteristics of the individual's skin, e.g., whether it is elastic and pliable, youthful, and other factors. Tissue expansion is based on the principle that skin and subdermal elements, including nervous tissue and vascular structures, stretch in response to expansion of an enlarging mass. The stretching results in an increase in surface area of the skin and other tissues. However, prior to the instant invention, there has been no concurrent pharmacological component of tissue expansion devices.

U.S. Pat. No. 2,499,045 to Walker et al., relates to an ano-rectal dilator and medicator. The invention consists of a tube with apertures, which is connected to an air inflation device, a bladder element enclosing the apertured portion of the tube, a non-expandable fabric form element that defines a maximum expansion size surrounding the bladder element, and a perforated resilient casing element surrounding the form element. A quantity of a treating agent can be interposed between the form element and the perforated casing element so that when the device is inflated, the treating agent is forced outwardly through the perforations and into contact with the affected areas of the rectal passage. The device does not include a chamber for holding the treatment agent, nor does it provide for replacing treating agent in situ.

U.S. Pat. No. 3,934,274 to Hartley, Jr., relates to a surgically implantable tissue augmentation prosthesis for mammary augmentation. The device comprises an outer sac and an inner capsule which is contained within the outer sac and occupies less than the entire volume of the outer sac. A gel or liquid is sealed within the inner capsule. The outer sac is filled with a liquid using a filling valve. Liquid in the outer sac may be withdrawn in order to deflate the prosthesis in response to spherical contracture.

U.S. Pat. No. 4,685,447 to Iversen et al., relates to a tissue expander system including a flat one-piece molded tissue expander, a connecting tube, and an injection port. A piece of non-stick fluorocarbon material can be used to prevent sticking of the tissue expander material during expansion. A Dacron mesh can be embedded in the tissue expander to provide for directional expansion.

U.S. Pat. No. 4,800,901 to Rosenberg, relates to a balloon type tissue expander which is inflated through a tube connected to the balloon and extending through an opening in the skin. In addition, there is a separate drain tube attached to or surrounding the inflation tube. The drain tube allows fluid, which may accumulate at the implantation site, to exit through an opening in the skin. An irrigation tube which is connected to the drain tube or inside the drain tube may also be included. This permits an irrigating liquid to be introduced into the implantation site of the balloon.

U.S. Pat. No. 4,984,585 to Austad, relates to a tissue expander comprised of an inflatable envelope, which can be separably mounted on a more rigid base, and a connector tube system which introduces fluid into the envelope. This invention provides for cutting the base into any desired shape, and conforming the expandable envelope to that shape.

U.S. Pat. No. 5,005,591 to Austad, relates to a self-inflating tissue expander. The tissue expander has a window portion which is highly permeable to extracellular water, however, the remaining portion is generally impermeable to water. The expander contains an osmotic agent that absorbs extracellular water. Absorption of water causes inflation of the implant.

Adjunctive Agents to Facilitate Rapid Tissue Expansion by Netscher et al. (Ann. Plast. Surg. 23:412, 1989), relates to a study of the effects of hyaluronidase, colchicine and prostaglandin $E_2$ on tissue expansion using rodent models. The agents were delivered into the tissue surrounding the implanted tissue expander by use of an intravenous catheter mounted on the circumference of the tissue expander. Infusion of a chemical agent was entirely independent of the expansion process.

The citation of any reference herein should not be deemed an admission that such reference is available as prior art to the invention.

SUMMARY OF THE INVENTION

The inventor has recognized a need in the art for an integrated tissue expander-expansion promoter delivery system to provide for greater comfort as well as facilitate and improve tissue expansion procedures.

Accordingly, the present invention provides a dual chamber tissue expansion device for subcutaneous implantation and delivery of a tissue expansion promoter in a patient. The device comprises an implantable expansion and delivery means comprising an expandable outer bladder prepared from a porous material capable of discharging an infusion solution therethrough, which defines an infusion chamber; and an expandable inner bladder disposed within said outer bladder and prepared from a non-porous material, which defines an expansion chamber, said inner bladder serving to effectuate the majority of the expansion of said expansion and delivery means. The device also includes means for delivering said infusion solution adapted for location external to said patient in use, and in fluid registry with said outer bladder, and means for inflating said inner bladder adapted for location external to said patient in use, and in fluid registry with said inner bladder. Preferably, the device comprises means for preventing adhesion of the outer membrane of the expansion chamber to the inner wall of the infusion solution chamber, such as texturing of the surfaces of each bladder that may be in contact or by providing a mechanical spacing member.

After implantation of the device subcutaneously, an infusion solution can introduced and removed from the outer bladder or infusion chamber. This allows for replacement of one infusion solution with another rapidly, or for increasing or decreasing the infusion rate by controlling pressure. Furthermore, fluid that accumulates in the tissue in contact with the tissue expansion device can be removed by applying suction to the infusion chamber.

Inflation of the inner bladder, or expansion chamber, can be accomplished by introducing a fluid into the expansion chamber. Fluid can be removed from the expansion chamber to deflate the device, e.g., to decrease pressure or prior to removal.

In a preferred embodiment, said inner and outer bladders are attached to a substantially non-stretchable and non-expandable member. In this embodiment, expansion of the device occurs in all directions except those bounded by this non-stretchable and non-expandable member. Generally, upon implantation, this member, which may be termed a backplate, is placed in contact with tissue, such as muscle or bone, where expansion is not desired.

As the expansion fluid fills the expandable inner bladder, the non-porous material expands. This expansion exerts a pressure forcing the infusion solution out of the infusion solution chamber, through the expandable porous material, and into the tissue surrounding and in contact with the porous material. In another embodiment, injection of the infusion solution under pressure can force the infusion solution out of the infusion solution chamber, through the expandable porous material, and into the tissue surrounding and in contact with the porous material. The pressure on the infusion solution, whether by expansion of the expansion chamber or injection through the liquid transport means, provides one mechanism for controlling the rate and depth of infusion of the infusion solution into tissues. Moreover, infusion occurs into all of the tissue in contact with the porous material that makes up the wall of the infusion chamber of the expander, which is the expansile surface of the expander.

The present invention advantageously provides for infusion of a promoter of tissue expansion, i.e., one or more agents to facilitate the tissue expansion process. For example, the infusion solution may be saline or water for hydrodissection of the surrounding tissue. The infusion solution may contain an extracellular matrix digestive enzyme, such as hyaluronidase, that hydrolyzes one or more components of the extracellular matrix, which makes up the "glue" of the connective tissue; an anesthetic, such as lidocaine or bupivicaine, to relieve the pain associated with expansion; antibiotics, to prevent or treat an infection that may occur with any invasive procedure; a growth factor, in particular epidermal growth factor, to facilitate tissue growth following expansion; or an agent that inhibits one or more of the conditions of fibrosis, capsule formation, or scarring, such as a steroid, e.g., dexamethasone, or an anionic polymer, such as dextran sulfate. Two or more agents can be infused simultaneously or serially.

As noted above, the infusion chamber can serve as a reservoir for any accumulated liquid or fluid in the tissue around the expander. Such liquid or fluid will naturally flow through the pores of the porous material, and can be removed from the infusion chamber by applying suction through the liquid transport means (e.g., using the same means as for removing infusion solution). Applying suction to the infusion chamber will increase the rate of removal of accumulated liquid or fluid from the tissue.

In another embodiment, a drain may be inserted coaxially with, adjacent to, or in proximity to the infusion solution liquid transport means and the expansion fluid transport means for collection of accumulated fluid from around the expander and removal of the fluid from the tissue.

The present invention satisfies the need in this field for a tissue expansion device which permits various infusion solutions to be introduced into an implanted device without having to remove the device from the patient's body. The expansion of tissue can be very painful procedure. An advantage of the present invention is that it allows expansion to occur while simultaneously infusing the tissue area with, for example, anesthetic, to alleviate pain, hyaluronidase, to facilitate tissue dissection that accompanies expansion, or both. This advantage is important since the use of hyaluronidase can hasten the expansion process, and anesthetics can make the expansion process more comfortable for the patient. Furthermore, different infusion solutions can be used at different stages of the expansion process to augment each stage, for example, use of anesthetic upon insertion, a hydrolytic enzyme during expansion, and a growth factor to induce growth of the expanded skin. Infusion of such solutions is particularly beneficial when administered locally to all of the tissue in contact with the expansion device and with each subsequent expansion.

An object of this invention is to provide a device which expedites the expansion of tissue.

Another object of this invention is to provide a device which makes tissue expansion more comfortable for the patient.

Yet another object of the invention is to permit different infusion solutions to be introduced into all of the tissue in contact with the expanding wall of a tissue expander device requiring removal of the device.

BRIEF DESCRIPTION OF THE DRAWINGS

The invention may be better understood by reference to the drawings, which are schematic and are not drawn to scale.

DETAILED DESCRIPTION OF THE INVENTION

Figure 1A:
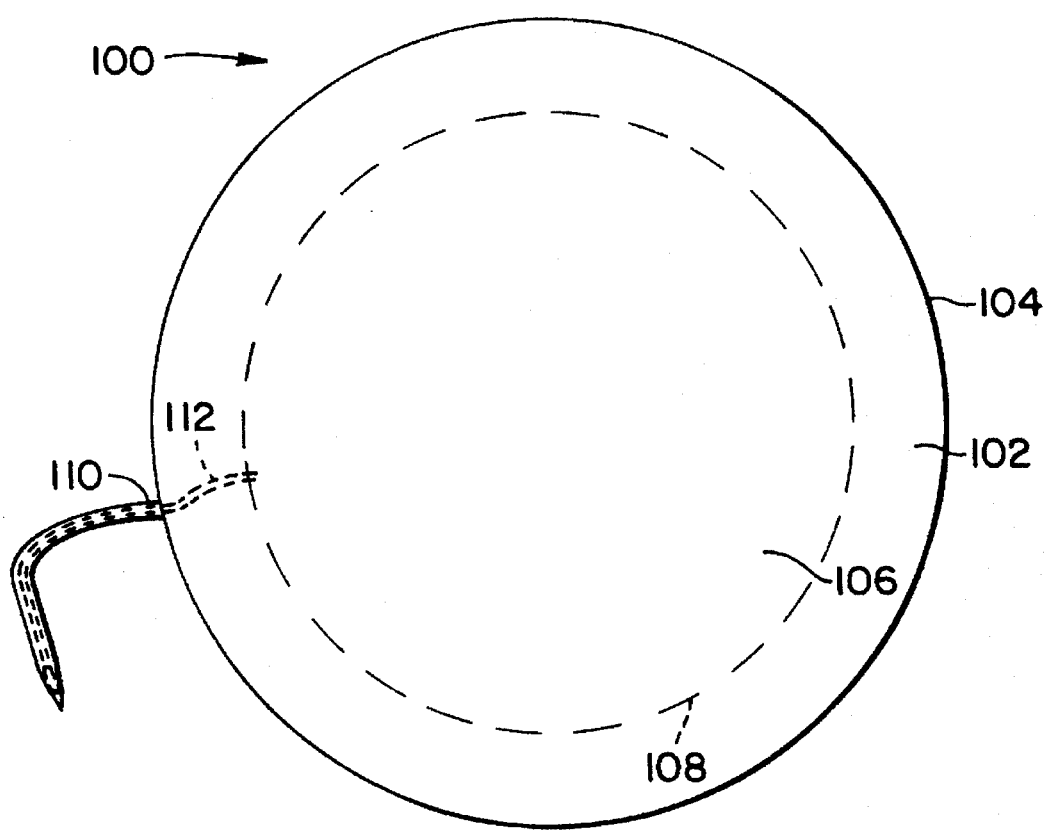
FIG. 1A is a schematic plan view of a specific embodiment of the DOUBLE CHAMBER TISSUE EXPANDER which is round and expands uniformly in all directions, i.e., spherically.

The present invention, for simultaneous expansion and delivery of a tissue expansion promotor to tissue, is comprised of an expandable infusion solution chamber (infusion chamber) which is defined by a stretchable porous material or wall. Within the infusion chamber is an inner bladder, i.e., an expansion fluid chamber (expansion chamber), which is isolated by a stretchable non-porous material, or wall, from the infusion chamber. Solutions are introduced and removed from the infusion chamber by a liquid transport means. Fluids are introduced and removed from the expansion chamber by a fluid transport means.

The term "tissue expansion" is used generally to describe the increase in tissue dimensions under the influence of a slowly enlarging mass beneath it. Tissue expansion may occur naturally or as a result of mechanical force. Natural tissue expansion occurs as a result of, for example, weight gain, tumor growth, and pregnancy. Tissue expansion by mechanical force is now a recognized modality of treatment in reconstructive surgery; as used herein, the term "tissue expansion" refers to expansion by mechanical force exerted by an implanted device.

As used herein, the term "hydrodissection" relates to the installation of an aqueous solution, such as saline or water, in soft tissues. The hydrodynamic force of the aqueous solution facilitates separation of the skin from the underlying tissue. Hydrodissection can facilitate open dissection, and can be implemented according to the instant invention to facilitate expansile dissections as well.

The outer bladder, or infusion chamber, is prepared from a stretchable non-porous material. The term "stretchable porous material" refers to a material which allows the infusion solution to pass from the infusion chamber into the tissue surrounding the implanted tissue expander, and which can stretch, i.e., increase its total area, during expansion of the device. The term "stretch" refers to the ability of the porous material to increase size in the dimensions of its plane; the material does not increase significantly in thickness, however. The rate of infusion can be controlled, in part, by choosing the number and size of the "pores" in the porous material. In one embodiment, the stretchable porous material has uniformly sized pores, e.g., produced in the material manufacturing process, that allow fluid to pass. Alternatively, the stretchable porous material may be a non-porous material that has been perforated, e.g., with a laser, pin or needle pricks, or by cutting. The expandable porous material should be biocompatible. In a preferred embodiment, the expandable porous material is prepared from perforated silicone rubber. Other expandable materials for use in surgical procedures and implantation in animals, particularly humans, may be used.

The porous material can be fabricated to contain pores or micropores, or it may be a non-porous material that is modified by puncturing to make small cuts, holes, or pores, e.g., with a needle. An advantage of using a porous material is that the pores create a surface texturing effect on the exterior of the implant. Surface texturing, or creating a roughened surface on an implant, helps prevent formation of a thickened capsule. Although this is not important to tissue expansion, it is important when such an expansion device is subsequently used as an implant.

The inner bladder, or expansion chamber, is prepared from a stretchable non-porous material. The term "stretchable non-porous material" refers to a material which is essentially non-porous, i.e., which prevents significant dispersion or diffusion of fluids through or across the material. Examples of suitable materials include silicone rubber, and derivatives thereof. Other suitable materials which are appropriate for surgical procedures and implantation in animals, particularly humans, may be used. "Stretchable" is used as defined above in connection with the non-porous material. The material should be strong enough to withstand expansion of the chamber without cracking or significant leaking.

According to the invention, the inner bladder and outer bladder do not adhere to each other. In a particular aspect, the invention provides means for preventing adhesion of the outer surface of the expansion chamber to the inner surface of the infusion chamber. For example, if the walls of both chambers are prepared from silicone rubber, upon contact the walls may adhere to each other. Preventing such adhesion can be achieved by manufacturing each chamber from materials that do not adhere to each other on contact. A means for preventing adherence is to prevent contact mechanically, e.g., with use of a mechanical spacing member. For example, appropriately sized, inert spheres or a matrix that fits between the chambers can be included. Alternatively, either the outer surface of the expansion chamber, or the inner surface of the infusion chamber, or both, can be textured.

As used herein, the term "infusion solution" refers to any solution introduced into the infusion chamber to be eluted from the pores of the porous membrane when sufficient pressure is exerted by the expanding non-porous material or by injection pressure. The infusion solution may contain one or more agents that can facilitate tissue expansion. Examples of such agents include antibiotics, anesthetics, extracellular matrix digestive enzymes, growth factors, e.g., epidermal growth factor (EGF), fibroblast growth factor (FGF), platelet-derived growth factor (PDGF), and angiogenic growth factor, and agents that inhibit fibrosis, capsule formation and/or scar formation.

Preferred antibiotics include those effective against staphylococci, such as but not limited to methicillin and vancomycin. Generally, antibiotics are administered prophylactically, since if a bacterial infection develops around the implanted expander, usually the expander is removed from the subject.

As used herein, the term "extracellular matrix digestive enzyme" refers to an enzyme that digests a component of the extracellular matrix. One such enzyme is hyaluronidase. Enzymes that digest glycosaminoglycans or proteoglycans, can also be used, such as, but not limited to, chondroitinase, keratanase, and the like.

As used herein, the term "agent that inhibits fibrosis, capsule formation, or scar formation" includes but is not limited to steroids, such as dexamethasone, and anionic polymers, such as dextran sulfate.

The term "expansion fluid" refers to any fluid introduced into the expansion solution chamber in order to expand the expandable non-porous material. Examples of suitable expansion solutions include, but are not limited to saline, buffered saline, water and air.

A specific embodiment of the invention is shown in FIG. 1A. The dual chamber tissue expansion device, 100, may be subcutaneously implanted within a patient. The device contains an infusion chamber, 102, defined by a stretchable porous material, 104; an expansion chamber, 106, located within the infusion chamber but isolated from the infusion chamber by a stretchable non-porous material, 108; an infusion solution liquid transport means, 110; and an expansion fluid transport means, 112. The infusion solution transport means and expansion fluid transport means may be silicon tubes, or other bio-compatible materials formed in tubular shape. In this embodiment, the infusion solution transport means and expansion fluid transport means are tube arranged coaxially, in which the expansion fluid tube, 112, is inside the infusion solution tube, 110.

Following implantation of the dual chamber tissue expander, expansion fluid is introduced to the expansion chamber through the expansion fluid transport means, 112. As the expansion chamber fills with expansion fluid, the expansion chamber, 106, expands, and the non-porous material, 108, stretches. The expansion fluid transport means, 112, may also be used to remove expansion fluid from the expansion solution chamber to facilitate removal of the dual chamber tissue expander, or reduce expansion pressure, if either are desired.

The pressure exerted by the expanding expansion chamber pressurizes the infusion solution, which is introduced to the infusion chamber, 102, through the infusion solution transport means, 110. In another embodiment of the invention, the pressure exerted by the injection of infusion solution into the infusion chamber, by use of the infusion solution transport means, pressurizes the infusion solution. In either cases, the infusion solution pressure forces the infusion solution through the porous material, 104, and into the tissues in contact with or proximal to the expander.

In a preferred embodiment of the present invention, the infusion solution is saline, to provide for hydrodissection of the connective tissue matrix. For example, the infused solutions may be 0.15M NaCl, or buffered 0.15M NaCl.

In other embodiments, lidocaine, hyaluronidase or both may be present in the infusion solution.

The infusion solution liquid transport means, 110, may also be used to remove an infusion solution from the infusion solution chamber, 102, if that is necessary. As a result, the infusion solution may be changed without removing the implanted dual chamber expander from the patient's body.

A particular advantage of the invention is the flexibility it provides with respect to the infusion of agents to facilitate tissue expansion. In particular, one or more agents can be infused together. Alternatively, different agents can be infused serially, if that is desired. For example, the initial infusion solution may comprise hyaluronidase and lidocaine in a buffered saline solution. This infusion solution would lead to hydrodissection and digestion of the connective tissue matrix, with local anesthesia to alleviate discomfort and pain. Additionally, in the immediate postoperative period, an antibiotic may be infused to prevent the onset of an infection. Finally, after the skin is stretched, infusion of a growth factor may provide for growth of new tissue, yielding a robust expanded tissue ready for use in reconstructive surgery.

Figure 1B:
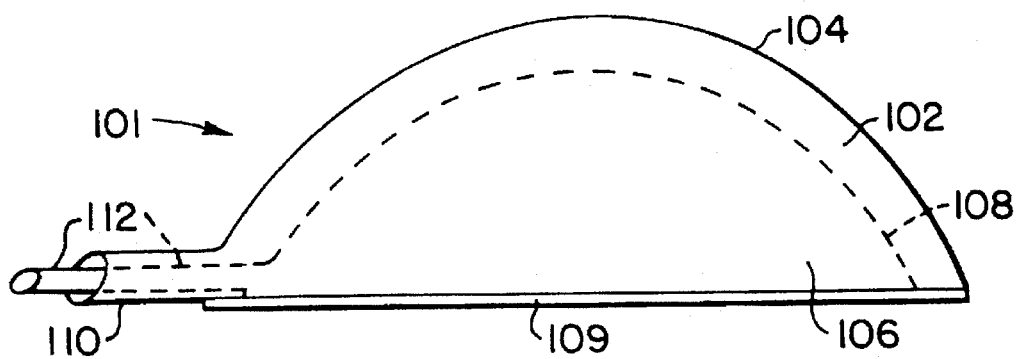
FIG. 1B is a full sectional side view of an alternate embodiment of the DOUBLE CHAMBER TISSUE EXPANDER having a backing member, which is round but expands hemispherically.

In another embodiment of the present invention, as shown FIG. 1B, the double chamber tissue expander device, 101, which includes a porous outer wall, 104, that defines the infusion chamber, 102, within which the expandable inner bladder prepared from a non-porous material, 108, which defines the expansion chamber, 106, is mounted to a rigid backplate, 109. The use of a backplate, 109, permits expansion in all direction except against the backplate, i.e., the device expands hemispherically. The backplate does not contain pores, so no infusion solution elutes in that direction. Examples of materials suitable for the backplate include a thick silicone material with fibrous synthetic mesh or net within the silicone to give strength and prevent stretching. In this embodiment, the expansion fluid transport means (tube), 112, is arranged coaxially within the infusion solution transport means (tube), 110.

Figure 2:
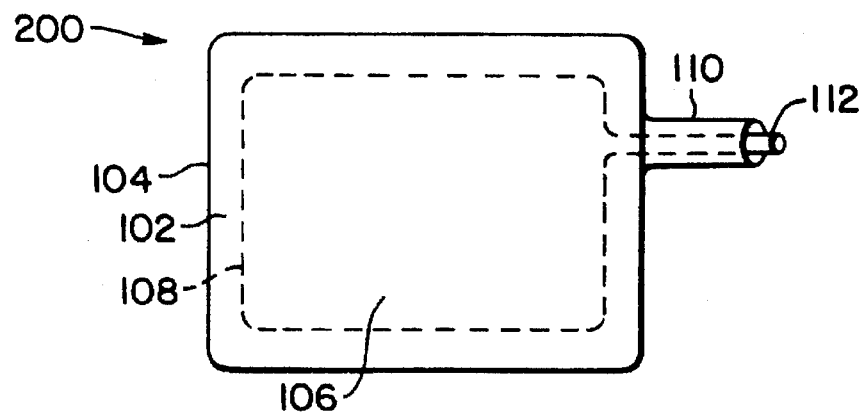
FIG. 2 is a schematic plan view of an embodiment of the invention in which the DOUBLE CHAMBER TISSUE EXPANDER has a square rectangular shape.
Figure 3:
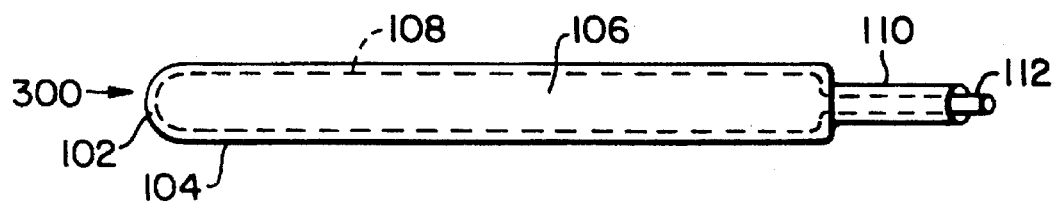
FIG. 3 is a schematic plan view of an embodiment of the invention in which the DOUBLE CHAMBER TISSUE EXPANDER has rod shape.
Figure 4:
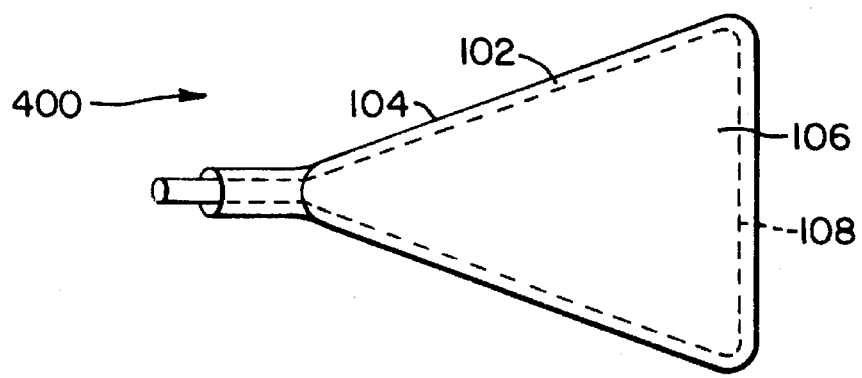
FIG. 4 is a schematic plan view of an embodiment of the invention in which the DOUBLE CHAMBER TISSUE EXPANDER has a triangular shape.

In addition to having a preferred round or circular shape yielding a sphere or hemisphere (if there is a backplate) upon inflation, a device of the invention may be square or rectangular, (FIG. 2), 200, rod shaped (FIG. 3), 300, or triangular (FIG. 4), 400. Such alternatives may be useful where the shape can provide an advantage. For example, a rod-shaped device can be used to expand tissue along the length of a limb, e.g., for reconstruction of a gash, burn or other injury running the length of the limb.

Figure 5A:
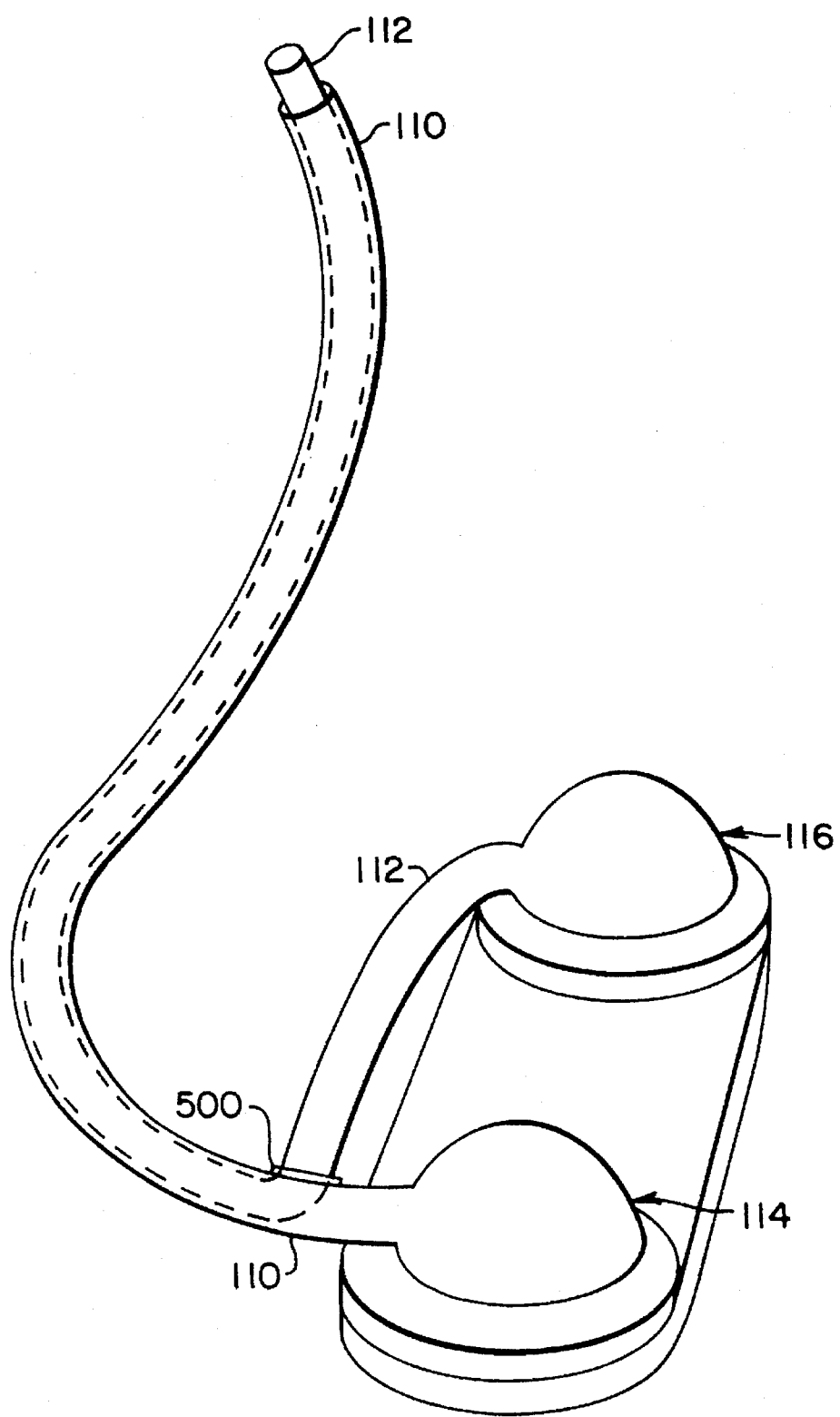
FIG. 5A is a schematic drawing of the infusion solution liquid transport means and the expansion fluid liquid transport means having separate injection ports, which are shown in a side view.

FIG. 5A is a detail drawing of the infusion solution liquid transport tube, 110, with infusion solution delivery means, which is an injection port, 114, and the expansion fluid transport tube, 112, with inflating means, which is a separate injection port, 116. One end of each tube is connected to the respective chamber (not shown here). The other end is connected to an injection port, e.g., as described in U.S. Pat. No. 4,685,447 to Iversen et at., which is specifically incorporated herein by reference. The tubes are adapted to pass through an opening in the skin when the device is implanted. In FIG. 5A, the injection ports, 114 and 116, are separate. In this embodiment, the tubes are arranged coaxially. Therefore, sealing means, 500, are provided to allow for exit of the internal expansion fluid tube to connect to its injection port without causing a leak in the injection solution tube. For example, the tubes can be heat sealed, or a sealant, such as silicone, applied to form a seal.

Figure 5B:
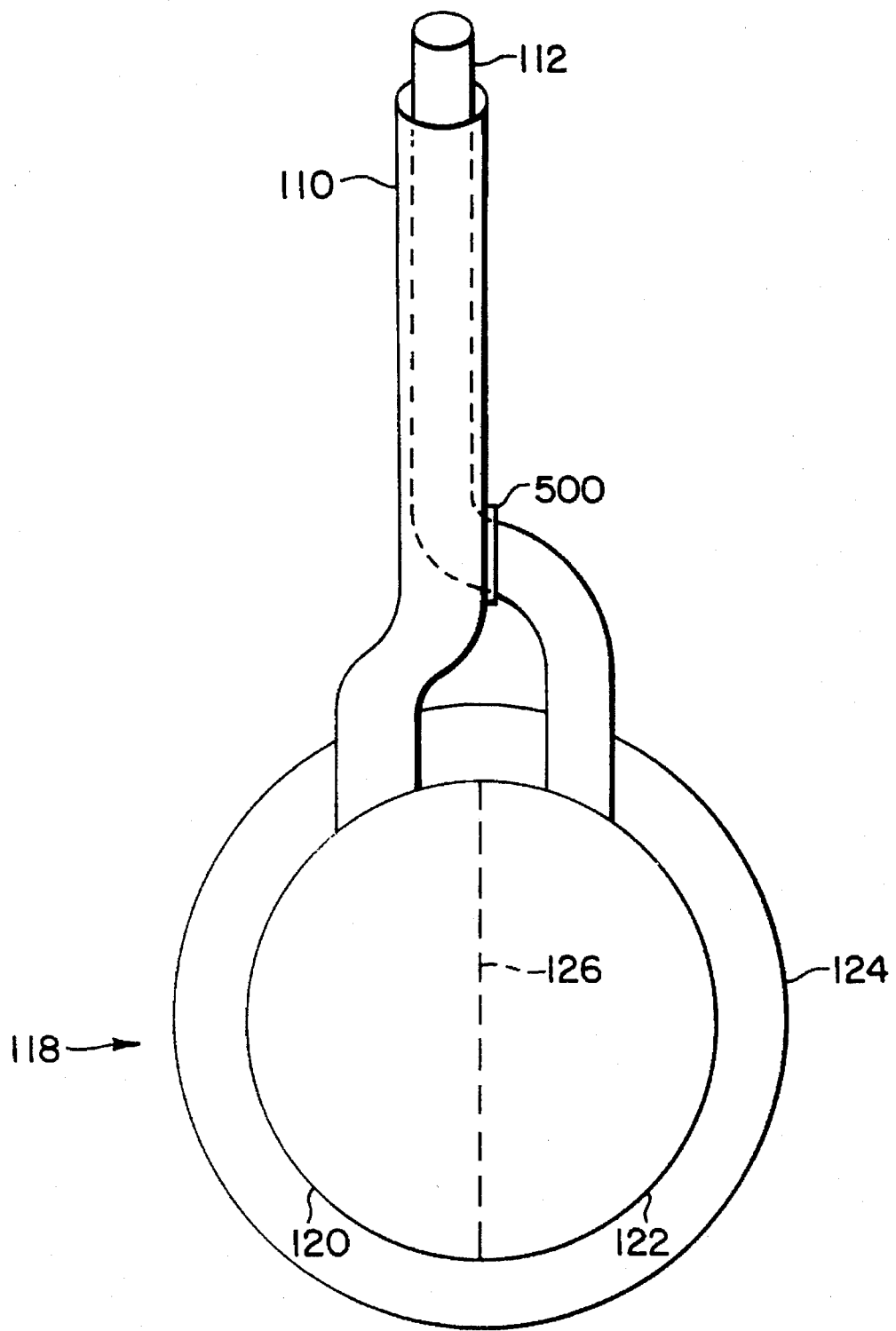
FIG. 5B is a schematic drawing of an embodiment in which there is a single injection port, shown in plan view, having a single hemisphere divided by a wall providing for separate injection of the infusion solution and the expansion fluid.

FIG. 5B is another embodiment, wherein a single injection port, 118, having two separate hemispheres, one for injection or withdrawal of an infusion solution, 120, and another for injection or withdrawal of an expansion fluid, 122, mounted on a base, 124, is used. Such a dual injection port can be prepared by modifying a single injection port by including a wall, 126, fabricated from the same material as the bulb of the injection port, dividing the hemisphere in half. Again, since the tubes are arranged coaxially, sealing means, 500, as described above, are provided.

Figure 6A:
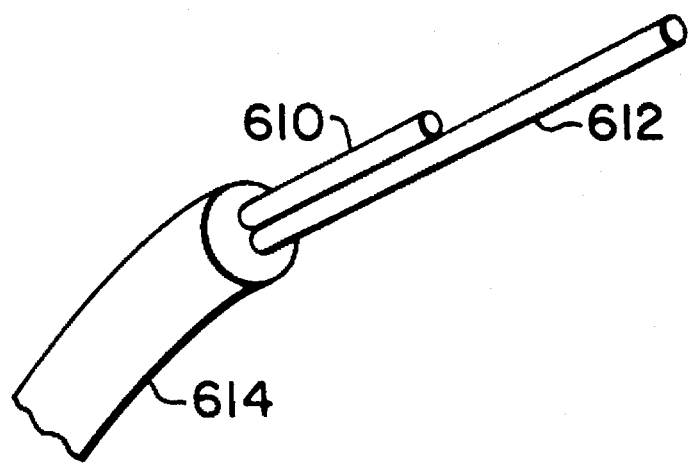
FIG. 6A is a schematic drawing of an embodiment wherein the tube for the infusion solution liquid transport means and the tube for the expansive fluid transport means are encased in an outer sleeve.

FIG. 6A is a detail drawing of one embodiment wherein the infusion solution tube, 610, and the expansion fluid tube, 612, are encased in an outer sleeve, 614. The outer sleeve provides for contact of a single surface with the skin opening through which the tubes extend. Accordingly, the outer sleeve must be prepared from a biocompatible material. An example of suitable outer sleeve material is silicone. Clearly, in this embodiment, no sealing means, as shown in FIGS. 5A and 5B, is required.

Figure 6B:
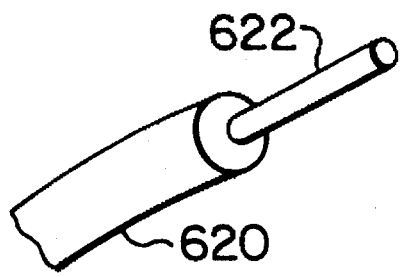
FIG. 6B is a schematic drawing of an embodiment wherein the expansion fluid tube is encased in infusion solution tube, i.e., the tubes are arranged coaxially.

FIG. 6B is another embodiment wherein the infusion solution tube, 620, is encases the expansion fluid tube, 622. This embodiment is shown in FIGS. 1-5 as well.

The specific embodiments disclosed above are not intended to limit the present invention. It is recognized that changes may be made in the process and apparatus specifically described herein without departing from the scope and teachings of the present invention.

Various publications and patents are cited in the Specification, each of which is specifically incorporated herein in its entirety.

What is claimed is:

1. A tissue expansion device for subcutaneous implantation and delivery of a tissue expansion promoter in a patient comprising:

an expansion and delivery means for subcutaneous implantation and tissue expansion comprising an expandable outer bladder prepared from a stretchable porous material capable of discharging an infusion solution therethrough, and an expandable inner bladder disposed within said outer bladder and prepared from a stretchable non-porous material, which inner bladder and outer bladder are non-adherent, said inner bladder serving to effectuate the majority of the expansion of said expansion and delivery means;

wherein said inner and outer bladders are attached to a substantially non-stretchable and non-expandable rigid backplate member;

means for delivering said infusion solution adapted for location external to said patient in use, and in fluid communication with an interior of said outer bladder; and means for inflating said inner bladder adapted for location external to said patient in use, and in fluid communication with an interior of said inner bladder.

2. The device of claim 1 further including means for preventing adhesion of the inner bladder to the outer bladder.

3. The device of claim 1 further including first liquid transport means associated with said infusion solution delivering means, for delivering said infusion solution to said outer bladder, and a second fluid transport means associated with said inflating means for introducing and removing an expansion fluid into and out of said inner bladder.

4. The tissue expansion device according to claim 1 in which the stretchable porous material is perforated silicone.

5. The tissue expansion device according to claim 1 wherein said outer bladder contains an infusion solution, and said infusion solution comprises an agent selected from the group consisting of an antibiotic, an anesthetic, an extracellular matrix digestive enzyme, a growth factor, and an agent that inhibits one or more of the conditions of fibrosis, capsule formation, or scar formation.

6. The tissue expansion device according to claim 1 in which said outer bladder contains an infusion solution selected from the group consisting of water, buffered saline, and saline.

7. The tissue expansion device according to claim 1 in which stretchable non-porous material is silicone.

8. The tissue expansion device according to claim 1 wherein said inner bladder contains an expansion fluid selected from the group consisting of buffered saline, saline, water, and air.

9. The tissue expansion device according to claim 1 in which said infusion solution delivery means is tubular wherein one end is in liquid communication with the interior of said outer bladder, and the opposite end extends to a first injection port.

10. The tissue expansion device according to claim 1 in which said inflating means is tubular wherein one end is in fluid communication with the interior of said inner bladder, and the opposite end extends to a second injection port.

11. The tissue expansion device according to claim 1 in which said infusion solution delivery means is tubular wherein one end is in liquid communication with the interior of said outer bladder and the opposite end extends to a first injection port; and the inflation means is tubular wherein one end is in fluid communication with the interior of said inner bladder and the opposite end extends to second injection port.

12. The liquid transport means of claim 11 in which said inflation means is located co-axially inside said infusion solution delivery means.

13. The tissue expansion device of claim 1 which is round.

14. The tissue expansion devise of claim 13 which is round.

* * * * *